(12) United States Patent
Batton

(10) Patent No.: US 9,585,816 B2
(45) Date of Patent: Mar. 7, 2017

(54) EFFERVESCENT TABLET FOR ELIMINATION OF RED WINE DISCOLORATION, OFFENSIVE ODOUR OF MOUTH AND CLEANING THE PALATE

(71) Applicant: Lynette Batton, Greensboro, NC (US)

(72) Inventor: Lynette Batton, Greensboro, NC (US)

( * ) Notice: Subject to any disclaimer, the term of this patent is extended or adjusted under 35 U.S.C. 154(b) by 0 days.

(21) Appl. No.: 14/728,308

(22) Filed: Jun. 2, 2015

(65) Prior Publication Data

US 2015/0366764 A1 Dec. 24, 2015

Related U.S. Application Data

(60) Provisional application No. 62/149,525, filed on Apr. 18, 2015.

(51) Int. Cl.

| | | |
|---|---|---|
| *A61K 8/02* | (2006.01) | |
| *A61K 8/24* | (2006.01) | |
| *A61K 8/365* | (2006.01) | |
| *A61K 8/60* | (2006.01) | |
| *A61K 8/73* | (2006.01) | |
| *A61K 8/81* | (2006.01) | |
| *A61K 8/97* | (2006.01) | |
| *A61Q 11/00* | (2006.01) | |
| *A61K 8/34* | (2006.01) | |
| *A61K 8/36* | (2006.01) | |
| *A61K 8/19* | (2006.01) | |

(52) U.S. Cl.
CPC .......... *A61K 8/0216* (2013.01); *A61K 8/022* (2013.01); *A61K 8/19* (2013.01); *A61K 8/345* (2013.01); *A61K 8/361* (2013.01); *A61K 8/365* (2013.01); *A61K 8/731* (2013.01); *A61Q 11/00* (2013.01); *A61K 2800/222* (2013.01)

(58) Field of Classification Search
CPC ........ A61K 8/0216; A61K 8/365; A61K 8/19; A61K 8/361; A61K 8/731; A61K 8/022; A61K 8/345; A61K 2800/222; A61Q 11/00
See application file for complete search history.

(56) References Cited

U.S. PATENT DOCUMENTS

| | | | | |
|---|---|---|---|---|
| 4,687,662 | A * | 8/1987 | Schobel | A61K 9/0007 424/44 |
| 5,807,578 | A * | 9/1998 | Acosta-Cuello | A61K 9/0007 424/441 |
| 2003/0170301 | A1* | 9/2003 | Wehling | A23L 1/302 424/466 |
| 2010/0034889 | A1* | 2/2010 | Rau | A23L 2/395 424/489 |
| 2010/0285158 | A1* | 11/2010 | Aldritt | A61K 36/45 424/732 |

FOREIGN PATENT DOCUMENTS

TR    EP 2722037 A1 *  4/2014  ......... A61K 9/1617

* cited by examiner

*Primary Examiner* — Anoop Singh
*Assistant Examiner* — Doan Phan
(74) *Attorney, Agent, or Firm* — Barry Choobin; Patent 360

(57) ABSTRACT

The embodiments herein discloses a composition and method for the synthesis of an effervescence producing tablet for reducing and eliminating a mouth odor and oral staining caused by ingested beverages and food. The method comprises mixing excipients, disintegrating agents, flavor and sweetener in a V-blender. The lubricant is added V-blender to obtain a mixture. The mixture is compressed on tablet press equipment with a round tooling. The tablets are packaged in a foil pouch. The "excipients" in the effervescent tablet composition are malic acid, sorbitol, potassium bi-carbonate, microcrystalline cellulose, sodium chloride, sodium carbonate and magnesium oxide. The malic acid react with potassium bicarbonate or sodium bicarbonate or sodium carbonate to form an effervescence reaction to induce tablet disintegration, provide a pleasant sensation in the mouth, and to clean a wine stain in the mouth.

7 Claims, 1 Drawing Sheet

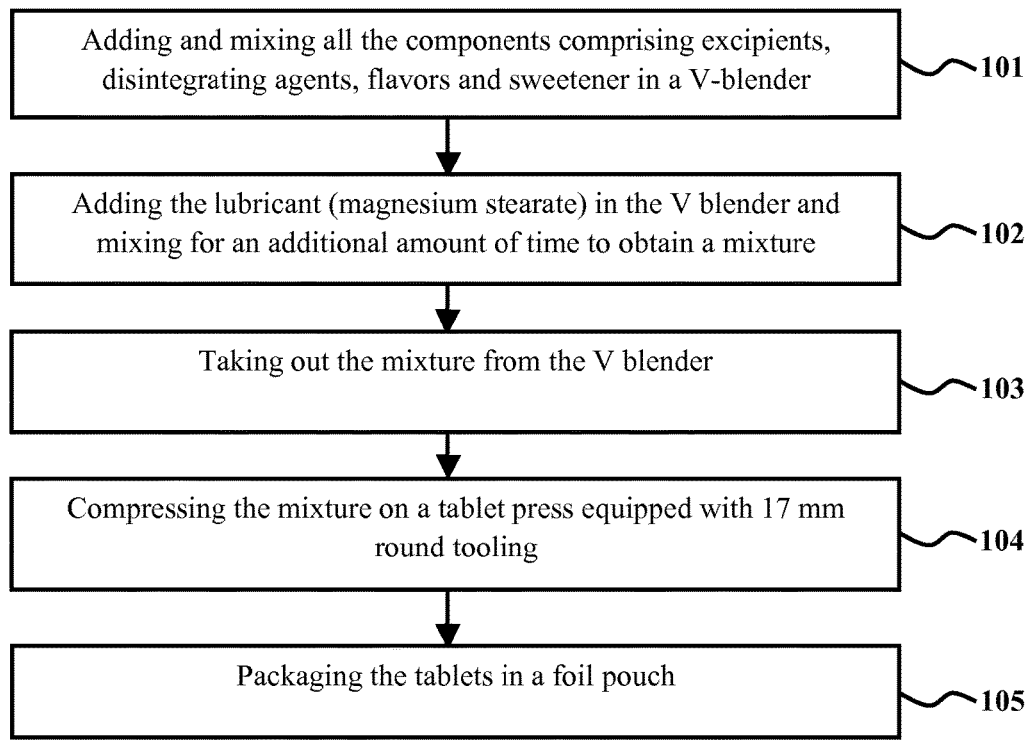

EFFERVESCENT TABLET FOR ELIMINATION OF RED WINE DISCOLORATION, OFFENSIVE ODOUR OF MOUTH AND CLEANING THE PALATE

BACKGROUND

Technical Field

The embodiments herein generally relate to a field of health care products. The embodiment herein particularly relate to an oral care tablet. The embodiments herein more particularly relate to an effervescent tablet for eliminating oral cavity discoloration and bad odor.

Description of the Related Art

The mouth is the first portion of the alimentary canal that receives food and has salivary glands. The oral mucosa is the mucous membrane epithelium which provides the lining to the inner portion of the mouth. The oral cavity consists of two regions. They are the vestibule and the oral cavity proper. The vestibule is the area between the teeth, lips and cheeks. The oral cavity is bounded at the sides and in front by the alveolar process (comprising the teeth) and at the back by the isthmus of the fauces. The floor of the oral cavity has tongue. Mucous membrane lines the sides and under surface of the tongue to the gum lining the inner aspect of the jaw mandible. The secretions are received from the submaxillary and sublingual salivary gland.

Oral and maxillofacial pathology is also termed as dental disease or oral pathology or mouth disease that are referred to disease of the mouth, jaws and related structures such as salivary glands, temporomandibular joints, facial muscles and periodontal skin. Mouth is full of bacteria. These bacteria along with mucus, food particles and ingested beverages form a sticky, colorless "plaque" on teeth. Plaque that is not removed by cleaning or brushing, hardens and forms "tartar". Only a professional cleaning by a dentist or dental hygienist can removes tartar.

In absence of oral hygiene, the problems such as gingivitis, periodontitis, bad breadth, discoloration of oral cavity/ teeth arise. The food particles or the beverages remain in the mouth, promoting microbial growth between teeth around the gums and on the tongue. This causes bad breadth.

The peripheral growth stimuli for harmful oral bacteria are residual food and food sugars coupled with the natural moisture and temperature condition of the mouth. Under such conditions these stimuli provide for explosive growth of harmful bacteria. These oral bacteria secrete acidic residues which further worsen the oral health. The oral bacteria induce dental caries and periodontal disease.

Decaying food particles or remains of beverages which are trapped between teeth, gum area and on the tooth enamel, are inconvenient or difficult to remove. This further contributes to higher levels of acidity in mouth and poor health of teeth, dental caries and induce periodontal disease.

Red wine is a tasty mix of natural dyes, acids and tannins. These three ingredients work together to etch and stain teeth. The red wine staining teeth is mostly a coating of dyed saliva. There are long-term dulling effects from a chronic diet of dark acidic wines. The acids in the wine actually affect the tooth enamel. Hence it is not recommended to brush immediately after drinking wine. The softened teeth enamel gets eroded by brushing. Further it has been reported that the remains of wine, after drinking causes tooth erosion. As the wine is extremely acidic in nature. The acids present in the wine erode tooth enamel, and creates rough spots or grooves on tooth surface. This leaves the teeth open to stains from other food or drinks.

Compounds designed to clean the oral cavity and provide fresh breath are well known. Generically such compounds fall into two grouping, dentifrices and mouth washes. The other compounds are generally described as breath mints or breathe freshener which may be delivered in gums. Further liquids, sprays or small pill like shapes are not considered oral cavity cleaners.

Mouthwashes are over the counter solutions containing varying amounts of alcohol. Alcohol is used in mouthwash preparation as a solvent in which other additions such as anti-microbial agents, flavouring oils, color additives, fluoride and astringents are dissolved and caused to react in water based solution. For many such additives agents, alcohol is preferred. Also the alcohol is chemically and economically accepted.

Utilizing alcohol in an oral hygiene preparation have many detrimental effects depending upon the user. Besides generating potential medical and health problems, its inclusion in oral hygiene products also presents potential social implications for some users. The medical implications of using alcohol in an oral hygiene preparation are validated by providing an explicit warning label on alcohol based mouthwashes along with the corrective actions to be taken in case of two much mouth wash is ingested.

Hence there is a need for a composition comprising an orally usable medicinal component and effervescent component. Also there is a need to synthesize an oral administrable composition which dissolves in the oral cavity. Further there is a need to synthesize an oral tablet for cleaning oral palate/oral cavity and breathe freshening.

The above mentioned shortcomings, disadvantages and problems are addressed herein and which will be understood by reading and studying the following specification.

OBJECTIVES OF THE EMBODIMENTS

The primary objective of the embodiments herein is to synthesize an effervescence producing tablet for cleaning oral palate and oral stains caused due to the remains of the food particles and ingested beverages.

Another object of the embodiments herein is to synthesize an effervescence producing tablet for avoiding bad mouth odor.

Yet another object of the embodiments herein is to provide an effervescence producing tablet which disintegrates automatically when the tablet comes into contact with the moisture in mouth.

Yet another object of the embodiments herein is to provide an effervescence producing tablet which provides freshness after getting dissolved in mouth.

Yet another object of the embodiments herein is to provide an effervescence producing tablet which removes and reduces oral discoloration caused by beverages.

Yet another object of the embodiments herein is to provide an effervescence producing tablet which is non-alcoholic in nature.

Yet another object of the embodiments herein is to provide an effervescence producing tablet which is ingestible without any side effects.

These objects and the other advantages of the embodiments herein will become readily apparent from the following detailed description taken in conjunction with the accompanying drawings.

SUMMARY

The various embodiments herein provide an effervescence producing tablet effective for bad breath, cleaning and disinfecting mouth, teeth and gums. The embodiments also provide the composition comprising surface acting agents or surfactants to act as solvent. These surfactants eliminate the need for alcohol and enabling the use of flavoring agents and coloring additives.

According to one embodiment herein, the embodiments herein provides an orally dissolving effervescent tablet for reduction and elimination of red wine discoloration of mouth and lips while or after drinking red wine. Further the effervescent tablet aids in cleaning the palate and reduces and eliminates offensive mouth odor in mouth.

According to one embodiment herein, an effervescent tablet composition for eliminating red wine discoloration of mouth, offensive odour of mouth and for cleaning the palate comprises an excipient, a disintegrating agent, a flavouring agent, a sweetener, an active agent and a lubricant.

According to one embodiment herein, the excipient comprises a malic acid, a F-melt, a sorbitol, a sodium bicarbonate, a potassium bicarbonate, a microcrystalline cellulose, a sodium chloride, a sodium carbonate and a magnesium oxide. The quantity of the malic acid present in the composition is 25-35% w/w. The quantity of the F-melt present in the composition is 15-25% w/w. The quantity of the sorbitol present in the composition is 10-15% w/w. The quantity of the sodium bicarbonate present in the composition is 3-8% w/w. The quantity of the potassium bicarbonate present in the composition is 3-8% w/w. The quantity of the microcrystalline cellulose present in the composition is 2-7% w/w. The quantity of the sodium chloride present in the composition is 0-5% w/w. The quantity of the sodium carbonate present in the composition is 0-3% w/w. The quantity of the magnesium oxide present in the composition is 0-1% w/w. The F-melt comprises of rice starch and di-basic calcium phosphate.

According to one embodiment herein, the disintegrating agent is crospovidone, and the quantity of crospovidone present in the composition is 7-15% w/w. The flavouring agent is a natural flavouring agent and the flavouring agent is present in the composition is 3-8% w/w. The sweetener comprises a stevia leaf extract and a sucralose. The amount of stevia leaf extract present in the composition is 2-7% w/w and the quantity of sucralose present in the composition is 0-3% w/w. The malic acid acts both as an active ingredient and as an excipient. The lubricant is a magnesium stearate and the quantity of the magnesium stearate present in the composition is 0-3% w/w. The malic acid reacts with potassium bicarbonate or sodium bicarbonate or sodium carbonate to form an effervescence reaction.

According to one embodiment herein, the effervescence induces tablet disintegration and the effervescence provides a pleasing sensation in the mouth when dissolved.

According to one embodiment herein, the effervescence of the tablet assists in the disintegration of the tablet. The effervescence produced by the tablet provides freshness to the mouth. The effervescence cleanses the wine stain in the mouth.

According to one embodiment herein, a method of synthesizing an effervescent tablet for eliminating red wine discoloration of mouth, offensive odour of mouth and for cleaning the palate, comprises the following steps. The first step is mixing excipient, disintegrating agent, flavouring agent, sweetener, and active agent in a V-blender. Lubricant is added to the V-blender. The excipient, disintegrating agent, flavouring agent, sweetener, active agent and lubricant are mixed in the V-blender for 25-40 minutes for obtaining a homogenous composition. After mixing, the homogenous composition is collected from the blender. The homogenous composition mixture is compressed on a tablet press equipment with a round tooling. The tablet is packaged in a foil pouch.

According to one embodiment herein, the tablet press equipment has a 17 mm round tooling.

According to one embodiment herein, the excipient comprises malic acid, F-melt, sorbitol, sodium bicarbonate, potassium bicarbonate, microcrystalline cellulose, sodium chloride, sodium carbonate and magnesium oxide. The quantity of the malic acid present in the composition is 25-35% w/w. The quantity of the F-melt present in the composition is 15-25% w/w. The quantity of the sorbitol present in the composition is 10-15% w/w. The quantity of the sodium bicarbonate present in the composition is 3-8% w/w. The quantity of the potassium bicarbonate present in the composition is 3-8% w/w. The quantity of the microcrystalline cellulose present in the composition is 2-7% w/w. The quantity of the sodium chloride present in the composition is 0-5% w/w, and wherein a quantity of the sodium carbonate present in the composition is 0-3% w/w. The quantity of the magnesium oxide present in the composition is 0-1% w/w. The F-melt comprises of a rice starch and a di-basic calcium phosphate.

According to one embodiment herein, the disintegrating agent is crospovidone, and the quantity of crospovidone present in the composition is 7-15% w/w. The flavouring agent is a natural flavouring agent and the amount of flavouring agent present in the composition is 3-8% w/w. The sweetener comprises a stevia leaf extract and a sucralose. The amount of stevia leaf extract present in the composition is 2-7% w/w. The quantity of sucralose present in the composition is 0-3% w/w. The malic acid acts both as an active ingredient and as an excipient. The lubricant is a magnesium stearate, and quantity of the magnesium stearate present in the composition is 0-3% w/w. The malic acid reacts with potassium bicarbonate or sodium bicarbonate or sodium carbonate to form an effervescence reaction.

According to one embodiment herein, the effervescent tablet comprises of the following main components of excipient, disintegrating agent, flavor, sweetener, an active agent and lubricant.

The "excipient" in the effervescent tablet composition are malic acid, F-melt (rice starch and dibasic calcium phosphate), sorbitol, sodium bicarbonate, potassium bicarbonate, microcrystalline cellulose, sodium chloride, sodium carbonate and magnesium oxide. The "disintegrating agent" in the composition are crospovidone. The flavoring agent in the composition is natural flavoring agent. The sweeteners in the composition are stevia leaf extract and sucralose. Further the lubricant in the composition is magnesium stearate. The active agent in the composition is malic acid.

According to one embodiment herein, the amount or quantity of the ingredients present in the effervescent tablet are as follows. The malic acid is present in an amount of 25-35% w/w. The malic acid is an active ingredient and an excipient. The amount or quantity of other excipients in the effervescent tablet is malic acid 25-35% w/w, F-melt (rice starch and dibasic calcium phosphate) 15-25% w/w, sorbitol 10-15% w/w, sodium bicarbonate 3-8% w/w, potassium bicarbonate 3-8% w/w, microcrystalline cellulose 2-7% w/w, sodium chloride 0-5% w/w, sodium carbonate 0-3% w/w and magnesium oxide 0-1% w/w. The rice starch and dibasic calcium phosphate also act as disintegrating agent.

The amount or quantity of the disintegrating agent crospovidone is 7-15% w/w. The amount or quantity of the flavoring agent or natural flavoring agent is 3-8% w/w. The amount or quantity of the sweetener is stevia leaf extract 2-7% w/w and sucralose 0-3% w/w. The amount or quantity of the lubricant is 0-3% w/w. The lubricant is magnesium stearate.

According to one embodiment herein, the method of synthesizing the effervescent tablet for bad mouth odor and cleaning palate comprises the following steps. The first step is mixing all the components except for magnesium stearate in a V-blender. The next step is adding the magnesium stearate to the V-blender and mixing for an additional amount of time to obtain a mixture. The time of mixing is 25 to 40 minutes. The mixture is taken out from the blender. The mixture is compressed on tablet press equipment with 17 mm round tooling. Further the tablets are packaged in a foil pouch.

According to one embodiment herein, the effervescent reactions occur between potassium bicarbonate and malic acid, sodium bicarbonate and malic acid and sodium carbonate and malic acid. The effervescence enhances tablet disintegration and provides a pleasing sensation in the mouth when dissolved. The effervescence of the tablet assists in the disintegration of the tablet more quickly. Further the effervescence provides freshness to the mouth. The effervescence cleanses the wine stain in the mouth.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIG. 1 illustrates a flowchart indicating a method for synthesizing the effervescent tablet for cleaning palate and oral stains caused by food particles and ingested beverages, according to an embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

According to one embodiment herein, the composition provides an orally dissolving effervescent tablet for reduction and elimination of red wine discoloration of mouth and lips while or after drinking red wine. Further the effervescent tablet aids in cleaning the palate and reduces and eliminates offensive mouth odor in mouth.

According to one embodiment herein, an effervescent tablet composition for eliminating red wine discoloration of mouth, offensive odour of mouth and for cleaning the palate comprises an excipient, a disintegrating agent, a flavouring agent, a sweetener, an active agent and a lubricant.

According to one embodiment herein, the excipient comprises a malic acid, a F-melt, a sorbitol, a sodium bicarbonate, a potassium bicarbonate, a microcrystalline cellulose, a sodium chloride, a sodium carbonate and a magnesium oxide. The quantity of the malic acid present in the composition is 25-35% w/w. The quantity of the F-melt present in the composition is 15-25% w/w. The quantity of the sorbitol present in the composition is 10-15% w/w. The quantity of the sodium bicarbonate present in the composition is 3-8% w/w. The quantity of the potassium bicarbonate present in the composition is 3-8% w/w. The quantity of the microcrystalline cellulose present in the composition is 2-7% w/w. The quantity of the sodium chloride present in the composition is 0-5% w/w. The quantity of the sodium carbonate present in the composition is 0-3% w/w. The quantity of the magnesium oxide present in the composition is 0-1% w/w. The F-melt comprises of rice starch and di-basic calcium phosphate.

According to one embodiment herein, the disintegrating agent is crospovidone, and quantity of crospovidone present in the composition is 7-15% w/w. The flavouring agent is a natural flavouring agent and the flavouring agent is present in the composition is 3-8% w/w. The sweetener comprises a stevia leaf extract and a sucralose. The amount of stevia leaf extract present in the composition is 2-7% w/w, and the quantity of sucralose present in the composition is 0-3% w/w. The malic acid acts both as an active ingredient and as an excipient. The lubricant is a magnesium stearate, and the quantity of the magnesium stearate present in the composition is 0-3% w/w. The malic acid reacts with potassium bicarbonate or sodium bicarbonate or sodium carbonate to form an effervescence reaction.

According to one embodiment herein, the effervescence induces tablet disintegration and the effervescence provides a pleasing sensation in the mouth when dissolved.

According to one embodiment herein, the effervescence of the tablet assists in the disintegration of the tablet. The effervescence produced by the tablet provides freshness to the mouth. The effervescence cleanses the wine stain in the mouth.

According to one embodiment herein, a method of synthesizing an effervescent tablet for eliminating red wine discoloration of mouth, offensive odour of mouth and for cleaning the palate, comprises the following steps. The first step is mixing excipient, disintegrating agent, flavouring agent, sweetener, and active agent in a V-blender. The lubricant is added to the V-blender. The excipient, disintegrating agent, flavouring agent, sweetener, active agent and lubricant are mixed in the V-blender for 25-40 minutes for obtaining a homogenous composition. After mixing, the homogenous composition is collected from the blender. The homogenous composition mixture is compressed on a tablet press equipment with a round tooling. The tablet is packaged in a foil pouch.

According to one embodiment herein, the tablet press equipment has a 17 mm round tooling.

According to one embodiment herein, the excipient comprises malic acid, F-melt, sorbitol, sodium bicarbonate, potassium bicarbonate, microcrystalline cellulose, sodium chloride, sodium carbonate and magnesium oxide. The quantity of the malic acid present in the composition is 25-35% w/w. The quantity of the F-melt present in the composition is 15-25% w/w. The quantity of the sorbitol present in the composition is 10-15% w/w. The quantity of the sodium bicarbonate present in the composition is 3-8% w/w. The quantity of the potassium bicarbonate present in the composition is 3-8% w/w. The quantity of the microcrystalline cellulose present in the composition is 2-7% w/w. The quantity of the sodium chloride present in the composition is 0-5% w/w, and wherein a quantity of the sodium carbonate present in the composition is 0-3% w/w. The quantity of the magnesium oxide present in the composition is 0-1% w/w. The F-melt comprises of a rice starch and a di-basic calcium phosphate.

According to one embodiment herein, the disintegrating agent is crospovidone, and the quantity of crospovidone present in the composition is 7-15% w/w. The flavouring agent is a natural flavouring agent and the amount of flavouring agent present in the composition is 3-8% w/w. The sweetener comprises a stevia leaf extract and a sucralose. The amount of stevia leaf extract present in the composition is 2-7% w/w. The quantity of sucralose present in the composition is 0-3% w/w. The malic acid acts both as an active ingredient and as an excipient. The lubricant is a magnesium stearate, and quantity of the magnesium stearate present in the composition is 0-3% w/w. The malic acid reacts with potassium bicarbonate or sodium bicarbonate or sodium carbonate to form an effervescence reaction.

According to one embodiment herein, the effervescent tablet comprises of the following main components. The main components are excipient, disintegrating agent, flavor, sweetener and lubricant.

The "excipient" in the effervescent tablet composition are malic acid, F-melt (rice starch and dibasic calcium phosphate), sorbitol, sodium bicarbonate, potassium bicarbonate, microcrystalline cellulose, sodium chloride, sodium carbonate and magnesium oxide. The "disintegrating agent" in the composition are crospovidone. The flavouring agent in the composition is natural flavouring agent. The sweeteners in the composition are stevia leaf extract and sucralose. Further the lubricant in the composition is magnesium stearate. The active agent in the composition is malic acid.

According to one embodiment herein, the amount or quantity of the ingredients present in the effervescent tablet are as follows. The malic acid is present in an amount of 25-35% w/w. The malic acid is an active ingredient and an excipient. The amount or quantity of other excipients in the effervescent tablet is malic acid 25-35% w/w, F-melt (rice starch and dibasic calcium phosphate) 15-25% w/w, sorbitol 10-15% w/w, sodium bicarbonate 3-8% w/w, potassium bicarbonate 3-8% w/w, microcrystalline cellulose 2-7% w/w, sodium chloride 0-5% w/w, sodium carbonate 0-3% w/w and magnesium oxide 0-1% w/w. The rice starch and dibasic calcium phosphate also act as disintegrating agent.

The amount or quantity of the disintegrating agent crospovidone is 7-15% w/w. The amount or quantity of the flavoring agent or natural flavoring agent is 3-8% w/w. The amount or quantity of the sweetener is stevia leaf extract 2-7% w/w and sucralose 0-3% w/w. The amount or quantity of the lubricant is 0-3% w/w. The lubricant is magnesium stearate.

According to one embodiment herein, the method of synthesizing the effervescent tablet for bad mouth odor and cleaning palate comprises the following steps. The first step is mixing all the components i.e. excipient, disintegrating agent, flavor and sweetener except for the lubricant (magnesium stearate) in a V-blender. The next step is adding the lubricant (magnesium stearate) to the V-blender and mixing for 25-40 minutes. The mixture is taken out from the blender. The mixture is compressed on tablet press equipment with 17 mm round tooling. Further the tablets are packaged in a foil pouch.

According to one embodiment herein, the effervescent reactions occur between potassium bicarbonate and malic acid, sodium bicarbonate and malic acid, sodium carbonate and malic acid. The effervescence enhances tablet disintegration and provides a pleasing sensation in the mouth when dissolved. The effervescence of the tablet assists in the disintegration of the tablet more quickly. Further the effervescence produced by the tablet provides freshness to the mouth. The effervescence cleanses the wine stain in the mouth.

FIG. 1 illustrates a flowchart indicating a method for synthesizing the effervescent tablet for cleaning palate and oral stains caused by food particles and ingested beverages, according to an embodiment herein. With respect to FIG. 1, the first step is adding and mixing all the components comprising excipients, disintegrating agents, flavors and sweetener in a V-blender except lubricant (101). The lubricant (magnesium stearate) is added in the V blender and mixed for an additional amount of time to obtain a mixture (102). Further the mixture is taken out from the V blender (103). The mixture is compressed on tablet equipped with 17 mm round tooling (104). The tablet is packaged in a foil pouch (105).

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. An effervescent tablet composition for eliminating red wine discoloration of mouth, offensive odor of the mouth and for cleaning a palate comprises an excipient, a disintegrating agent, a flavoring agent, a sweetener, an active agent, and a lubricant;

wherein the excipient comprises a malic acid, a combination comprising a rice starch and a di-basic calcium phosphate, a sorbitol, a sodium bicarbonate, a potassium bicarbonate, a microcrystalline cellulose, a sodium chloride, a sodium carbonate and a magnesium oxide;

wherein the malic acid is present in the composition in a range of 25-35% w/w, the combination comprising the rice starch and the di-basic calcium phosphate is present in the composition in a range of 15-25% w/w, the sorbitol is present in the composition in a range of 10-15% w/w, the sodium bicarbonate is present in the composition in a range of 3-8% w/w, the potassium bicarbonate is present in the composition in a range of 3-8% w/w, the microcrystalline cellulose is present in the composition in a range of 2-7% w/w, the sodium chloride is present in the composition at less than or equal to 5% w/w, the sodium carbonate is present in the composition at less than or equal to 3% w/w, the magnesium oxide is present in the composition at less than or equal to 1% w/w, the flavoring agent is a natural flavoring agent and is present in the composition is 3-8% w/w, the lubricant is a magnesium stearate and is present in the composition at less than or equal to 3% w/w, the sweetener comprises a stevia leaf extract and a sucralose, and the stevia leaf extract is present in the composition in a range of 2-7% w/w and the sucralose is present in the composition is in a range of 0.1-3% w/w; and wherein the malic acid reacts with potassium bicarbonate or sodium bicarbonate or sodium carbonate to form an effervescence reaction to induce tablet disintegration, to provide a pleasant sensation in the mouth when dissolved, and to clean a wine stain in the mouth.

2. The composition according to claim 1, wherein the disintegrating agent is crospovidone, and wherein a quantity of crospovidone present in the composition is 7-15% w/w.

3. The composition according to claim 1, wherein the malic acid acts both as an active ingredient and as an excipient.

4. A method of producing an effervescent tablet for eliminating red wine discoloration of mouth, offensive odor of mouth and for cleaning the palate, the method comprises the steps of:
a) mixing an excipient, a disintegrating agent, a flavoring agent, a sweetener and an active agent in a V-blender;
b) adding a lubricant to the V-blender;
c) further mixing the excipient, the disintegrant agent, the flavoring agent, the sweetener, the active agent and the lubricant in the V-blender for 25-40 minutes for obtaining a homogenous composition;
d) collecting the homogenous composition from the blender;
e) compressing the homogenous composition mixture on a tablet press equipment with a round tooling; and
f) packaging the tablet in a foil pouch;

wherein the excipient comprises a malic acid, a combination comprising a rice starch and a di-basic calcium phosphate, a sorbitol, a sodium bicarbonate, a potassium bicarbonate, a microcrystalline cellulose, a sodium chloride, a sodium carbonate and a magnesium oxide;

wherein the malic acid is present in the composition in a range of 25-35% w/w, the combination comprising the rice starch and the di-basic calcium phosphate is present in the composition in a range of 15-25% w/w, the sorbitol is present in the composition in a range of 10-15% w/w, the sodium bicarbonate is present in the composition in a range of 3-8% w/w, the potassium bicarbonate is present in the composition in a range of 3-8% w/w, the microcrystalline cellulose is present in the composition in a range of 2-7% w/w, the sodium chloride is present in the composition at less than or equal to 5% w/w, the sodium carbonate is present in the composition at less than or equal to 3% w/w, the magnesium oxide is present in the composition at less than or equal to 1% w/w, the flavoring agent is a natural flavoring agent and is present in the composition is 3-8% w/w, the lubricant is a magnesium stearate and is present in the composition at less than or equal to 3% w/w, the sweetener comprises a stevia leaf extract and a sucralose, and the stevia leaf extract is present in the composition in a range of 2-7% w/w and the sucralose is present in the composition is in a range of 0.1-3% w/w; and wherein the malic acid reacts with potassium bicarbonate or sodium bicarbonate or sodium carbonate to form an effervescence reaction to induce tablet disintegration, to provide a pleasant sensation in the mouth when dissolved, and to clean a wine stain in the mouth.

5. The method according to claim 4, wherein the tablet press equipment has a 17 mm round tooling.

6. The method according to claim 4, wherein the disintegrating agent is crospovidone, and wherein a quantity of crospovidone present in the composition is 7-15% w/w.

7. The method according to claim 4, wherein the malic acid acts both as an active ingredient and as an excipient.

* * * * *